Figure 1:
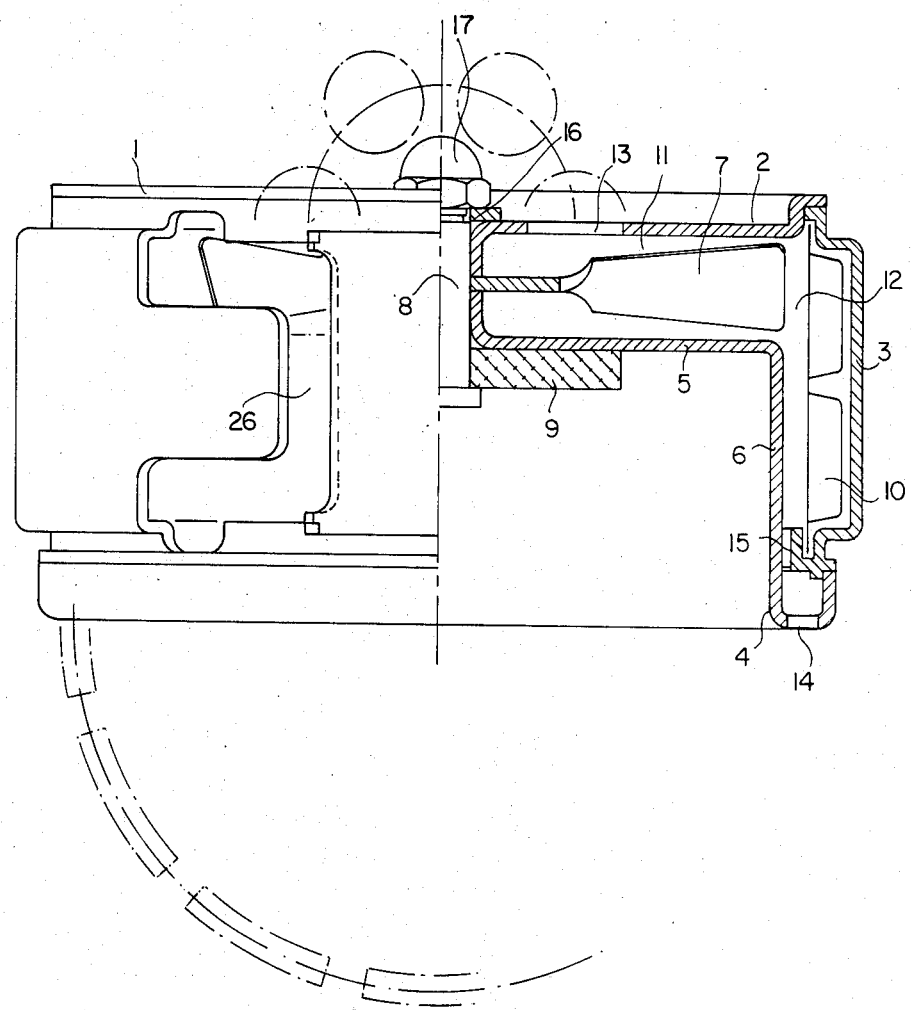

United States Patent [19]

Hempel et al.

[11] Patent Number: 4,663,293

[45] Date of Patent: May 5, 1987

[54] DEVICE FOR TESTING AIR FOR MICROORGANISM CONTENT

[75] Inventors: Hans D. Hempel, Mainaschaff; Dieter Merz, Frankfurt, both of Fed. Rep. of Germany

[73] Assignee: Biotest-Serum-Institut GmbH, Frankfurt, Fed. Rep. of Germany

[21] Appl. No.: 710,896

[22] Filed: Mar. 12, 1985

[30] Foreign Application Priority Data

Mar. 17, 1984 [DE] Fed. Rep. of Germany ....... 3410990

[51] Int. Cl.⁴ .............................................. C12M 1/28
[52] U.S. Cl. .................................... 435/294; 435/301
[58] Field of Search ................. 435/294, 300, 301, 30, 435/34

[56] References Cited

U.S. PATENT DOCUMENTS

| | | | |
|---|---|---|---|
| 3,127,329 | 2/1964 | Andersen | 435/294 X |
| 3,233,094 | 3/1966 | Teschner | 435/294 X |
| 3,684,660 | 8/1972 | Kereluk et al. | 435/294 |
| 3,968,012 | 7/1976 | Jones | 435/294 |
| 3,980,524 | 9/1976 | Reuter | 435/294 |

*Primary Examiner*—Alan Cohan
*Assistant Examiner*—John A. Rivell
*Attorney, Agent, or Firm*—Sprung Horn Kramer & Woods

[57] ABSTRACT

In a device for testing air for microorganism content with a rapidly rotating impeller inside a cylinder that has a backing sheet coated with culture medium against its inside surface, microorganisms that vary more extensively in size can be detected with almost equal effectiveness, the throughput of air can easily be determined, and the precipitation effect can be precisely tested because the backing sheet rotates along with the impeller, the blades of the propeller are at a low angle to the plane it rotates in, the air enters at a location that is separate from the location at which it leaves, through inlets from above and down and out through outlets, and the inner surface of the rotor below the impeller chamber is in the form of a channeling cylinder.

7 Claims, 3 Drawing Figures

DEVICE FOR TESTING AIR FOR MICROORGANISM CONTENT

BACKGROUND OF THE INVENTION

The present invention relates to a device for testing air for microorganism content.

The detection of microorganisms in the air is often of decisive significance in human and veterinary medicine and the pharmaceutical and food industries.

Many devices for this purpose are known. They function in accordance with various principles, are operated in accordance with different methods, and yield differing results both qualitatively and quantitatively.

A summary of a number of devices of this type can be found in *Air-Sampling Instruments for Evaluation of Atmospheric Contaminants*, 5th Edition (1978), American Conference on Governmental Industrial Hygienics.

Among the systems described in that publication are (1) the Anderson Sampler (pp. L-7 & O-20), the Sartorius Dust Accumulator (pp. L-19 & K-40), (3) the Casella and New Brunswick Slit Samplers (pp.O-12 & O-16), and (4) the so-called Stöber Centrifuge (pp. O-8 and O-9).

The drawbacks of devices (1)–(3) include their need for external electric power, their weight which makes them difficult to handle and transport, and the difficulty of keeping them sterile as a result of their size and complexity. Device (1) and (2) also require preparations that must be carried out in a clean room and devices (1) and (3) involve culture media in Petri dishes, which also complicates handling. None of the three devices works on the centrifuge principle.

Device (4) is the only one that operates on the centrifuge principle. It is, however, extremely difficult to handle and operate and cannot be routinely employed.

German Pat. No. 2 301 385 describes a device for testing air for its microorganism content that works on the centrifuge principle, handles a relatively large volume of air in a relatively brief time, and is small, easy to handle, and independent of external power sources. It also operates with a medium-coated backing sheet that can be cleanly and easily inserted into and extracted from the device. The device operates with a high-speed impeller with steeply angled blades positioned in the center of a rigid cylinder. The air is sucked in from above and forced against the backing sheet, which is mounted rigidly on the inside surface of the cylinder jacket. The air enters and leaves at the top through the same aperture.

In spite of the aforesaid advantages of this device, attempts have been made to improve the effectiveness and reliability with which it precipitates microorganisms of a wide range of sizes. Furthermore, a high level of turbulence (called a *Windhose*, "whirlwind" on page 4 of German Pat. No. 2,301,385) occurs upstream of the device when it is operated. Turbulence of course is undesirable in certain cases, in the vicinity of a surgical operation for instance and especially during osteological procedures, because of the risk of transmitting microorganisms. Finally, the throughput of air through the device cannot be precisely and readily determined.

The object of the present invention is to provide a device for testing air for microorganism content with all of the advantages of the device disclosed in German Pat. No. 2 301 385, meaning that it is small, easy to handle, portable, independent of external power sources, and can handle a large volume of air in a brief time, but that will be almost equally effective in capturing microorganisms of a wider range of sizes, that will exhibit little or no turbulence in operation, and that will have an air throughput that can easily be determined and a precipitation action that can be precisely tested and will accordingly represent a known dimension for the user.

This object is attained in accordance with the present invention by improving the known device which comprises a rapidly rotating impeller located in a channeling cylinder, means for blowing the air to be tested against an axially parallel layer of a culture medium, a motor independent of external power sources and connected in the top of a housing to the impeller through a driveshaft and a magnetic clutch, and a backing sheet coated with the culture medium, which is as long as the inside circumference of the cylinder and as wide as the cylinder is high, and having a tab that projects back out through a slot against the inside surface of the jacket of the cylinder. In accordance with the improvement the cylinder comprises a rotor which is powered by the motor through a shaft, and magnetic clutch and shaft, so as to rotate the impeller inside it and also the medium-coated backing sheet, the rotor has a channeling cylinder inside it that has a base at the top and in conjunction with at least part of the lid of the rotor constitutes an impeller chamber that is approximately $\frac{1}{3}$ to $\frac{1}{2}$ as high as the backing sheet is wide, the chamber accommodates the impeller, and has a jacket that extends down from the backing sheet by a slight distance there by defining an annular chamber between the backing sheet and the cylinder jacket, the rotor has separate air inlets and outlets, the air entering from above through the inlets and leaving downward through the outlets, either the outlets constitute a constricted zone in themselves or there is a constricted zone positioned upstream of them, and the blades of the impeller are positioned at a small angle relative to its plane of rotation.

It has been found that the following characteristics are essential to the invention to achieve its desired advatanges:

(1) the design of the impeller (2) the system in accordance with which the air is channeled, and (3) the accompanying rotation of the backing sheet.

The impeller must not only force the desired volume of air in but must also allow as little material as possible to adhere to it or be flung to the floor of the impeller chamber. It has been discovered that these prerequisites are fulfilled when the impeller blades are not positioned straight and steep in relation to the axis of the impeller but at a low angle to the plane in which it rotates. It is practical for the angle of the blades of the impeller to the plane in which it rotates to be between 15° and 40°, preferably between 20° and 25°.

An impeller of this type makes it possible to precipitate larger microorganisms onto the backing sheet very effectively. It has, however, been discovered that centrifugal force will not precipitate all the smaller and especially smallest microorganisms onto the backing sheet because of their lightweight. Air channeling accordingly plays a decisive role in precipitating the smaller microorganisms. The air must be channeled in such a way that each stream of air extends over the backing sheet to the same extent and at the same interval. No air at all must leave the device if at all possible without having It has been found that this prerequisite will be fulfilled if, on the one hand, the air enters and leaves at separate points, entering through inlets from above and leaving downwards through separate outlets and if, on the other hand, if the inner surface of the wall of the rotor below the impeller chamber constitutes a channeling cylinder, leaving a narrow annular chamber between the cylinder wall and the bottom of the backing sheet. The air will flow nonturbulently through the annular chamber between the outer surface of the cylinder and the backing sheet, with even the smallest microorganisms accordingly being able to precipitate onto the culture medium on the sheet.

Furthermore, a constricted zone upstream of the outlets retains the air in the device longer, increasing the probability that the smaller microorganisms will precipitate onto the culture medium. The constricted zone can consist either of a gap between the jacket of the channeling cylinder and the outer surface of the rotor jacket or of bores in the outer surface of the rotor jacket or at the junction between the surface and the jacket of the channeling cylinder.

Precipitation can be improved even more by also making the backing sheet rotate. The accompanying rotation of the backing sheet will prevent turbulence above the surface of the culture medium as a result of the motion of the impeller. A less turbulent flow of air will prevail inside the rotor, allowing uniform precipitation of the smaller microorganisms.

Other advantages of separating the inlets from the outlets are that there will be little or no turbulence above the device and that the throughput of air through the device can be easily and very precisely determined and hence the effectiveness of precipitation computed, providing the user with a definite and known figure.

The rotor rests on a preferably round housing and is powered by a motor inside the housing through a driveshaft and magnetic clutch, allowing the rotor to be sterilized due to its separation from the drive mechanism.

The motor is independent of external power sources and is powered by discardable or rechargeable batteries or storage batteries. Rechargeable sources are preferable. The series of batteries is preferably in the base of the housing to improve the heft of the device.

One preferred embodiment of the invention has electronic controls that maintain an essentially constant speed of rotation independent of the charge of the batteries. The controls also indicate when the charge is inadequate for satisfactory operation. They also exert a braking action on the relatively massive rotor, which would otherwise continue to rotate too long when the device is turned off.

The upper limit of the housing constitutes a motor mount with a combination motor and tachometer. The motor itself is enclosed in a hood for reasons of safety.

The medium-coated backing sheet is as long as the inside circumference of the rotor jacket and as wide as the rotor is high and has a tab at one end. It is preferably divided into individual depressions to facilitate counting the microorganisms, improve agar adhesion, and make the sheet more flexible. Before the commencement of operation the sterile sheet is inserted into the device through a slot with the tab left sticking out. The backing sheet corresponds essentially to that described in detail in German Pat. No. 2 301 385.

Figure 2:
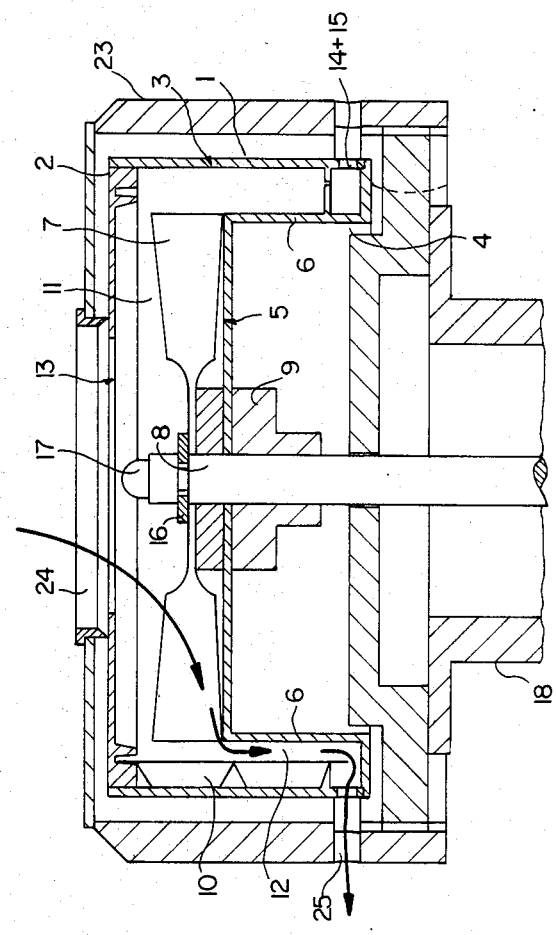
Figure 3:
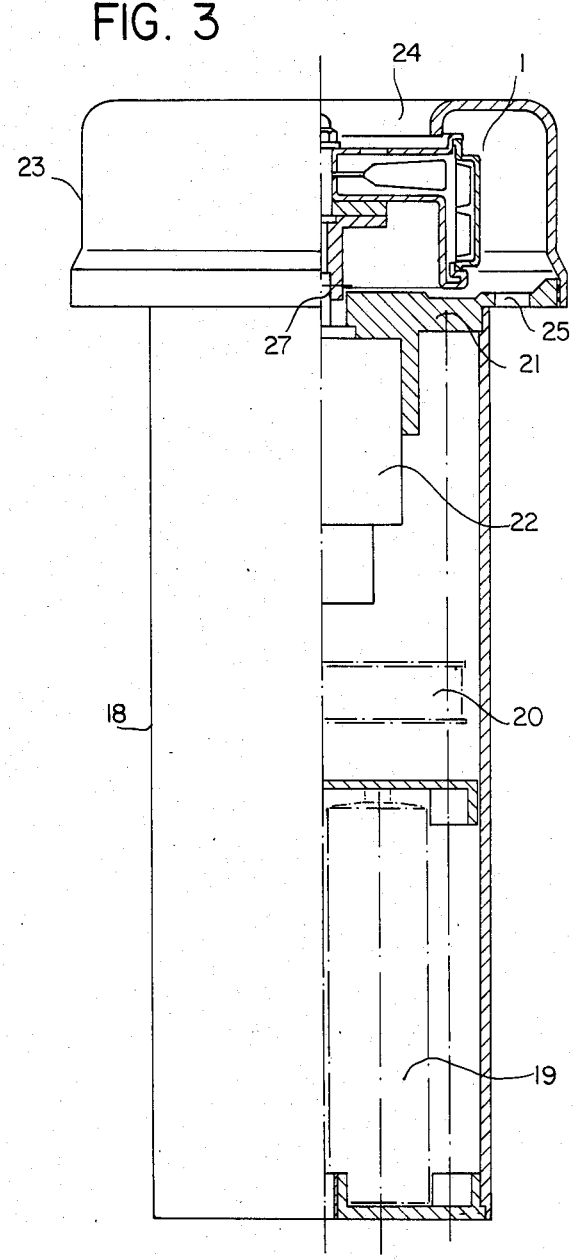

The invention will be further described with reference to the accompanying drawings, wherein FIG. 1 is a side elevation, partly in section, of one embodiment of a rotor of the invention, FIG. 2 is a vertical section through another embodiment of rotor, and FIG. 3 is a side elevation, partly in section, of the complete device with housing and protective hood.

FIG. 1 shows a rotor 1 with a lid 2 and a jacket 3 that has a channeling cylinder 4 consisting of a base 5 and of another jacket 6. Rotor lid 2 and cylinder base 5 constitute an impeller chamber 11 that accommodates an impeller 7 mounted on a driveshaft 8. Impeller chamber 11 is approximately ⅛ to ¼ as high as a backing sheet 10 is wide. Below impeller chamber 11 and in the vicinity of shaft 8 is a magnetic clutch 9. Backing sheet 10 extends along the inside surface of rotor jacket 3. Cylinder jacket 6 is spaced slightly from backing sheet 10, leaving an annular chamber 12. Annular chamber 12 is approximately 1 to 5 mm and preferably 1 to 3 mm wide. Below backing sheet 10, rotor jacket 3 and cylinder jacket 6 demarcate a constricted zone. Rotor lid 2 is provided with inlets 13 and the bottom of channeling cylinder 4 with outlets 14. All components of the rotor are fastened together by a cap nut 17. However, any other type of fastening, such as a rivet, soldering, or welding can also be employed. All that is essential is that the connection withstand the requisite temperatures because the material must be able to withstand steam at 120° and air at 180° C. for purposes of sterilization.

Below cap nut 17 is a washer 16 that transmits the force of the nut to rotor lid 2. Other methods of force transmission are of course also possible.

A slot 26 allows backing sheet 10 to be inserted.

FIG. 2 shows another type of rotor 1 with components 2 through 13, 16, and 17 that are essentially identical to those illustrated in FIG. 1. The rotor in FIG. 2 differs from that in FIG. 1, however, in that the constricted zone consists of outlets 14 themselves, which are bores in rotor jacket 3, with the air leaving laterally at the bottom of the jacket. It also shows the position of a safety hood 23, which also has inlets 24 and outlets 25.

FIG. 3 shows the preferably round housing 18 having a series 19 of throw-away or rechargeable batteries in its base. Above series 19 is a control electrode 20, which can also have operating mechanisms mounted on it. The top of housing 18 constitutes a motor mount 21, which not only accommodates a combination motor and tachometer 22 and a shaft 27 but also supports hood 23. Outlets 25 are located in the section of motor mount 21 that extends laterally over housing 18 and the air can flow through them when a rotor 1 of the type illustrated in FIG. 1 is employed. Rotor 1 is positioned below hood 23 with its inlets 24.

At the site where the air sample is to be obtained, a sterile backing sheet 10 coated with culture medium is inserted into the sterilized air-testing device through slot 26 in such a way that the medium-coated surface of the sheet faces impeller chamber 11 and annular chamber 12 and the sheet completely covers the inside circumference of rotor jacket 3, with the tab extending out of the slot. Rotor 1 is then coupled to the driveshaft 27 of combination motor and tachometer 22 with magnetic clutch 9 and safety hood 23 mounted.

The duration of operation or volume of air to be tested is set by means of a switch connected to electronic controls 20 and the starting button depressed. While the device is in operation, impeller 7 forces air into impeller chamber 11 through inlets 13 and hurls the air outward, with the larger microorganisms precipitating onto the culture medium on backing sheet 10. The air then flows down nonturbulently along with any smaller microorganisms remaining in it through the annular chamber 12 between backing sheet 10 and cylinder jacket 6. Choking structure 15 keeps the air in the device longer. Finally, the air exits down through outlets 14. Upon termination of the desired duration of operation and when rotor 1 stops, safety hood 23 is removed and backing sheet 10 is withdrawn by means of its tab, returned to its package, closed, and taken to the laboratory for culturing. To obtain further samples it is only necessary to insert a fresh sterile medium-coated backing sheet 10 into the device.

It will be understood that the specification and examples are illustrative but not limitative of the present invention and that other embodiments within the spirit and scope of the invention will suggest themseleves to those skilled in the art.

What is claimed is:

1. In a device for testing air for microorganism content, comprising a rapidly rotating impeller located in a jacketed channeling cylinder for blowing the air to be tested against an axially parallel layer of a culture medium, a motor independent of external power sources and connected in the top of a housing to the impeller through a driveshaft and a magnetic clutch, and a backing sheet coated with the culture medium, as long as the inside circumference of the cylinder and as wide as the cylinder is high, and having a tab that projects back out through a slot against the inside surface of the jacket of the cylinder, the improvement wherein the cylinder forms a rotor which is powered by the motor through the driveshaft and magnetic clutch, so as to rotate the impeller and also the medium-coated backing sheet, the rotor having a top and an internal channeling cylinder that has a base near the top and in conjunction with at least part of the top of the rotor constitutes an impeller chamber that is approximately $\frac{1}{3}$ to $\frac{1}{2}$ as high as the backing sheet is wide, the chamber accommodating the impeller, and having a jacket that extends down from the backing sheet by a slight distance, thereby defining an annular chamber between the backing sheet and the cylinder jacket, the rotor having separate air inlets and outlets, the air entering from above through the inlets and leaving downward through the outlets, either the outlets constituting a constricted zone in themselves or there being a constricted zone postitioned upstream of them, and the blades of the impeller being positioned at a small angle to its plane of rotation.

2. A device according to claim 1, wherein the angle of the blades of the impeller to the plane in which it rotates is between 15° and 40°.

3. A device according to claim 1, including a safety hood for the rotor.

4. A device according to claim 1, wherein the non-external power source is at least one battery in the base of the housing.

5. A device according to claim 4, wherein the battery is rechargeable.

6. A device according to claim 1, including electronic controls.

7. A device according to claim 1, including a mount for the motor.

* * * * *